United States Patent [19]

Pedersen

[11] 4,151,256

[45] Apr. 24, 1979

[54] WATER-IN-OIL DETECTION DEVICE

[75] Inventor: August B. Pedersen, East Horsley, England

[73] Assignee: Mobil Oil Corporation, New York, N.Y.

[21] Appl. No.: 904,100

[22] Filed: May 8, 1978

Related U.S. Application Data

[63] Continuation-in-part of Ser. No. 796,107, May 12, 1977, Pat. No. 4,089,652.

[51] Int. Cl.² .................... G01N 33/18; G01N 33/22
[52] U.S. Cl. .................................... 422/102; 422/103; 422/61; 422/50; 23/230 HC
[58] Field of Search ............. 23/230 HC, 253 R, 259, 23/292, 230 R, 232 R, 254 R

[56] References Cited

U.S. PATENT DOCUMENTS

| | | | |
|---|---|---|---|
| 3,019,342 | 1/1962 | Brooke | 23/230 HC |
| 3,528,775 | 9/1970 | O'Hara et al. | 23/230 HC |
| 3,833,340 | 9/1974 | Jones | 23/230 HC |
| 3,873,271 | 3/1975 | Young et al. | 23/230 HC |
| 3,976,572 | 8/1976 | Reick | 23/230 HC |
| 4,089,652 | 5/1978 | Pedersen | 23/230 R |

*Primary Examiner*—R. E. Serwin
*Attorney, Agent, or Firm*—Charles A. Huggett; Malcolm Keen

[57] ABSTRACT

A device for detecting the presence of small quantities of water in oil and other petroleum products comprises a container with an associated sample cup for a predetermined quantity of oil whose water content is to be measured, a collector vessel attached to the container and a delivery tube leading from the bottom of the container to the collector vessel. A valve may be interposed in the delivery tube so that the interior of the container can be completely sealed.

6 Claims, 2 Drawing Figures

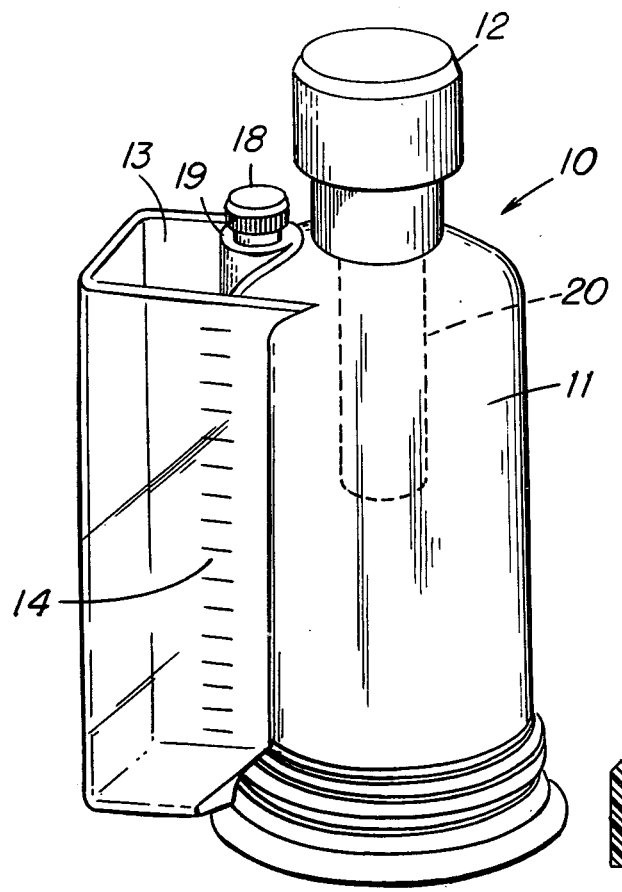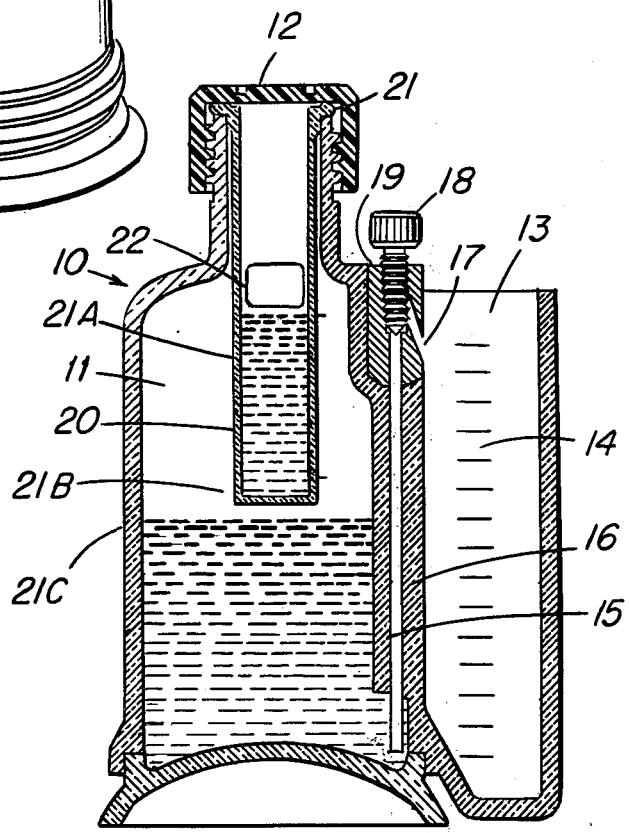

WATER-IN-OIL DETECTION DEVICE

CROSS-REFERENCE TO RELATED APPLICATIONS

Application Ser. No. 796,107 filed May 12, 1977 (now U.S. Pat. No. 4,089,652) of which the present application is a continuation-in-part.

The present application relates to a device for the detection of small amounts of water in petroleum oil products, for instance, lubricating oil which has been used in a marine diesel engine.

BACKGROUND OF THE INVENTION

During the operation of a marine diesel engine, the circulating lubricant generally becomes contaminated with water. The effective working life of the lubricant is limited by the accumulation of water, which, apart from altering the lubricant properties of the oil, may have a deleterious effect on the metal to be lubricated. Similar considerations arise with other uses of oils.

In order to determine whether the oil is suitable for further use of for regeneration or rejection, it is frequently necessary to know whether water is present in the oil in excess of a predetermined tolerated proportion. Such a proportion might be in the region of a few percent, e.g. 1 to 5 percent by weight of wet lubricant, but substantially higher water contents can be encountered. On the other hand, it may be desired to apply a more stringent standard, of a fraction of one percent.

In my co-pending application Ser. No. 796,107 (now U.S. Pat. No. 4,089,652) I have disclosed an improved method for providing a direct indication of the water content of an oil sample. The method, employing a simple form of apparatus can be used by unskilled operators and is capable of producing good results even when the water is present in a highly emulsified state in the oil.

The method comprises bringing a sample of the oil which is to be tested into contact with a reagent which is chemically inert to the oil but reactive with the water in the oil to produce a gas. The reagent is present in an inert liquid such as kerosine which is miscible with the oil sample. The pressure generated by the evolved gas is used to drive the inert liquid into a collector in which the amount expelled by the gas pressure can be estimated visually, either to obtain a numerical estimate of the water content or to determine whether the oil contains less or more than a predetermined amount of water.

SUMMARY OF THE INVENTION

I have now devised a convenient device for putting the test method into operation. The device is compact, neat and robust. It eliminates the need for levelling collector vessels and for having flexible, pendulous connecting tubes.

According to the present invention the detection device comprises a container with an associated sample cup for a predetermined quantity of oil whose water content is to be measured. The sample cup fits inside the container and can be removed for cleaning and filling through the mouth of the container. A collector vessel is attached to the container and a delivery tube leads from the bottom of the interior of the container to the collecting vessel. A valve is preferably provided in this delivery tube so that the interior of the container can be shut off from the exterior.

The container is sealed by a gas-tight closure e.g. a screw cap. The sample cup is contructed so that liquid in the container can be mixed with the oil sample in the cup.

BRIEF DESCRIPTION OF THE DRAWINGS

FIG. 1 is an isometric view of the device and

FIG. 2 is a vertical cross-section of the device, showing the liquids in place during the test.

DESCRIPTION OF PREFERRED EMBODIMENTS

The invention finds particular application in the testing of marine diesel-engine oil, and the apparatus of the invention is valuable and convenient as an accessory on board ship for routine oil testing. The invention is also useful for checking the water contents of oil from pipeline test stations, including crudes and refined products e.g. fuels.

The sample of oil subjected to test need not be large, in spite of the small quantities of water likely to be encountered. Typically, a sample of five milliliters is acceptable.

The substance reactive with water to produce gas is preferably calcium hydride, although other substances may be used such as calcium carbide, sodium hydride and so forth. The substance must be chemically inert to the oil under test and also to the manometric or measuring liquid miscible with the oil.

The liquid miscible with the oil under test, especially when the latter is marine engine lubricant, is most conveniently a petroleum hydrocarbon liquid, for example, kerosine, although other inert liquids miscible with the test oil may also be used, e.g. chlorinated hydrocarbons, oxygenated materials such as esters, ethers, polyolefins and so forth. The inert liquid should have a low vapor pressure, consistent with its use as a manometric liquid or measurer of gas volume. The quantity used is predetermined for the sake of reference level, but the amount is not otherwise critical.

Referring to the drawings, the apparatus 10 comprises a container 11 with a screw cap 12 which is suitably fabricated of a resilient plastic resin such as polyethylene, polypropylene or a polyamide. The cap may also be made of metal or another less resilient material, in which case it will desirably have an interior gasket to ensure that the container can be closed by the cap without any risk of gas or liquid leaking. The container itself may be fabricated of glass or a transparent plastic such as a polyacrylate e.g. Plexiglass or Lucite (trade marks) plastics.

Integral with container 11 is a collecting vessel 13 which has an engraved scale 14 on its side or sides. The scale may be engraved either in arbitrary units or directly in percentage readings for the water content of the oil. The collector 13 is open to the atmosphere.

A delivery tube or duct 15 extends vertically upwards through side wall 16 of container 11 with its integral collector 13 and opens into collector 13 at the top of the collector through a delivery port 17. A needle valve 18 is disposed in duct 15 so that the interior of the container can be shut off from the atmosphere. Valve 18 is suitably fabricated from a resilient plastic such as polypropylene or a polyamide with a metal seating 19 fixed in the body of container 11. The seating may suitably be fabricated of aluminum or stainless steel.

A sample cup 20 is suspended from the mouth of container 11 by an annular rim 21 which fits on top of the neck of the container and under cap 12. Being of plastic material e.g. polyethylene, polypropylene, it helps ensure a gas-tight closure of the container. A port 22 is let into the side of the cylindrical sample cup 20 to permit access between the interior of the sample cup and the interior of the container. Two engraved marks 21A and 21B on sample cup 20 indicate the levels for predetermined sample quantities. A mark 21C on the walls of container 11 indicates the level for the inert liquid. This mark is provided for convenience only. Its position is not critical.

In use, container 11 is filled to mark 21C with the inert liquid e.g. kerosine. The reagent is then mixed with the inert liquid with cap 11 off the container. This serves to remove residual water from the inert liquid. The reagent may be packaged in convenient dosage form e.g. in individual envelopes or capsules each of which contains enough reagent for one test.

A representative sample of the oil to be tested is then drawn and poured into sample cup 20 up to mark 21A. The filled sample cup is then inserted into container 11 and screw cap 12 screwed on tightly. Valve 18 is also closed tightly. The apparatus is then tilted and shaken so that the inert liquid (mixed with the reagent) and the oil sample become mixed through port 20. Agitation is suitably continued for about one minute after which the container 11 is returned to the upright position for about two minutes to allow a complete reaction between the reagent and any water present. After sufficient time has elapsed, valve 18 is opened. If the oil sample contained any water, it will have reacted with the reagent in the inert liquid to produce gas. The pressure generated above the surface of the liquid by the gas will drive the liquid out of container 11 by way of delivery tube 15, through delivery port 17 into collector 13. The greater the amount of water originally present in the sample, the greater will be the volume of gas generated and accordingly, a greater amount of liquid will be driven into collector 13. Thus, since a fixed sample of oil is used, collector 13 can be graduated directly in terms of the percentage of water present.

If the oil contains a large amount of water, all the inert liquid may be driven from container 11 into collector 13. In many circumstances this will provide sufficent evidence that excessive water is present in the oil but if it is desirable to determine the proportion of water more accurately, the test may be repeated, but this time filling the sample cup only to the level of mark 21B. Since the sample of oil will then be smaller, proportionately less gas will be generated and less of the inert liquid displaced. A separate series of numerical graduations can be provided on collector 13 for use when the sample cup is filled to mark 21B.

The control valve 18 with its associated delivery port 17 can, if desired, be positioned at the bottom of container 11 with a short delivery tube leading directly from the bottom of container 11 to the bottom of collector 13. In this case, however, either the valve head must protrude through the side or bottom walls of the container or the collector or a long-stemmed valve must be used.

After use, the device may be cleaned by flushing with a suitable liquid such as kerosine or gas oil.

I claim:

1. A testing device for detecting the presence of small quantities of water in petroleum products, which comprises:
   (i) a container for an inert liquid,
   (ii) a closure means for the container for providing a substantially gas-tight seal,
   (iii) a sample cup for containing a predetermined quantity of the petroleum product which is to be tested and having access to the interior of the container
   (iv) a collector integral with the container for receiving a quantity of the inert liquid expelled from the container by gas pressure in the container,
   (v) a delivery tube extending from the bottom of the interior of the container to the collector,
   (vi) a valve for controlling flow of the inert liquid through the delivery tube.

2. A testing device according to claim 1 in which the delivery tube extends from the bottom of the interior of the container upwards through a side wall of the container to a delivery port for the collector at the top of the collector.

3. A testing device according to claim 2 in which the valve is disposed at the top of the delivery tube.

4. A testing device according to claim 3 in which the valve comprises a screw valve.

5. A testing device according to claim 4 in which the valve comprises a movable screw member of resilient plastic material and a metal seating.

6. A testing device according to claim 1 in which the sample cup comprises a cylindrical vessel adapted to fit within the container and having a port in its side above its bottom to permit access between the interior of the container and the interior of the sample cup.

* * * * *